US009433736B2

(12) United States Patent
Smith et al.

(10) Patent No.: US 9,433,736 B2
(45) Date of Patent: Sep. 6, 2016

(54) POSITIONABLE ELONGATED MEMBERS WITH MULTI-AXIS JOINTS

(71) Applicants: Mathew S. Smith, Bend, OR (US); Douglas Randall Watson, Bend, OR (US)

(72) Inventors: Mathew S. Smith, Bend, OR (US); Douglas Randall Watson, Bend, OR (US)

(73) Assignee: JETTSTREAM, INC., Bend, OR (US)

(*) Notice: Subject to any disclaimer, the term of this patent is extended or adjusted under 35 U.S.C. 154(b) by 542 days.

(21) Appl. No.: 13/934,408

(22) Filed: Jul. 3, 2013

(65) Prior Publication Data

US 2015/0007810 A1 Jan. 8, 2015

(51) Int. Cl.
| | |
|---|---|
| *A61M 11/00* | (2006.01) |
| *A61M 15/00* | (2006.01) |
| *A61M 11/06* | (2006.01) |
| *B05B 11/00* | (2006.01) |
| *A61M 16/08* | (2006.01) |

(Continued)

(52) U.S. Cl.
CPC .............. *A61M 11/06* (2013.01); *A61M 15/00* (2013.01); *B05B 11/00* (2013.01); *A61M 16/0875* (2013.01); *A61M 2209/082* (2013.01); *A61M 2209/084* (2013.01); *F16M 11/105* (2013.01); *F16M 11/2064* (2013.01); *F16M 2200/022* (2013.01); *F16M 2200/08* (2013.01)

(58) Field of Classification Search
CPC .... A61M 11/06; A61M 11/00; A61M 15/00; A61M 16/0875; A61M 2209/082; A61M 2209/084; A61M 2209/08; A61M 2205/586; A61M 2205/587; A61M 2210/0618; B05B 11/00; B05B 7/0416; F16M 11/00; F21V 33/0068; F21V 21/28; F21V 21/26
USPC ....... 248/125.8, 122.1, 124.1, 125.7, 289.11, 248/291.1, 278.1, 288.31, 288.11; 128/200.21
See application file for complete search history.

(56) References Cited

U.S. PATENT DOCUMENTS

| | | | |
|---|---|---|---|
| 1,571,959 | A | 2/1926 | Mulligan |
| 2,419,860 | A | 4/1947 | Urrutia |
| 2,963,247 | A | 12/1960 | Collier |

(Continued)

FOREIGN PATENT DOCUMENTS

| | | |
|---|---|---|
| EP | 0585379 | 9/1998 |
| WO | 9927818 | 6/1999 |

(Continued)

OTHER PUBLICATIONS

Cumulus, Modern Ultrasonic Nebulizer, Heyer Medical AG, Nov. 2006.

(Continued)

*Primary Examiner* — Anita M King
(74) *Attorney, Agent, or Firm* — Leber Patent Law P.C.

(57) ABSTRACT

Devices are disclosed that include a positionable elongated member configured to support a delivery tube and maintain a distal end of the tube in a desired position and directional orientation, and to allow the position and orientation of the distal end of the tube to be adjusted by a user. The devices include a multi-segment elongated member configured to support a delivery tube and maintain a distal end of the tube in a desired position and orientation, and a multi-axis joint assembly disposed between segments of the elongated member to allow articulated relative movement of the segments. These devices may be used, for example, in the delivery of vaporized medicine to a patient, e.g., a child or infant on a bed.

26 Claims, 7 Drawing Sheets

(51) Int. Cl.
*F16M 11/10* (2006.01)
*F16M 11/20* (2006.01)

(56) References Cited

U.S. PATENT DOCUMENTS

| | | | |
|---|---|---|---|
| 3,089,028 A * | 5/1963 | Klampferer | F21S 6/003 |
| | | | 248/122.1 |
| 3,221,733 A | 12/1965 | Beasley | |
| 3,931,452 A | 1/1976 | Nilsson | |
| 3,971,538 A | 7/1976 | Marvich | |
| 4,020,834 A | 5/1977 | Bird | |
| 4,282,869 A | 8/1981 | Zidulka | |
| 4,321,917 A | 3/1982 | Campbell | |
| 4,338,924 A | 7/1982 | Bloom | |
| 4,461,292 A | 7/1984 | Montalbano | |
| 4,554,916 A | 11/1985 | Watt | |
| 4,593,688 A | 6/1986 | Payton | |
| 4,595,008 A | 6/1986 | Guibert | |
| 4,646,750 A | 3/1987 | Williams | |
| 4,679,551 A | 7/1987 | Anthony | |
| 4,732,147 A | 3/1988 | Fuller | |
| 4,863,133 A | 9/1989 | Bonnell | |
| 5,014,693 A | 5/1991 | Sauberli | |
| 5,092,551 A * | 3/1992 | Meier | F16M 11/14 |
| | | | 248/276.1 |
| 5,357,945 A | 10/1994 | Messina | |
| 5,609,565 A * | 3/1997 | Nakamura | 248/278.1 |
| 5,636,627 A | 6/1997 | Rochester | |
| 5,692,494 A | 12/1997 | Pernetti | |
| 5,941,839 A | 8/1999 | Ishikawa | |
| 6,065,473 A | 5/2000 | McCombs et al. | |
| 6,095,467 A * | 8/2000 | Neuhof | F16M 11/04 |
| | | | 248/278.1 |
| 6,224,027 B1 | 5/2001 | Johnson et al. | |
| 6,308,707 B1 | 10/2001 | Lu | |
| 6,371,115 B1 | 4/2002 | Cewers et al. | |
| 6,409,134 B1 * | 6/2002 | Oddsen, Jr. | F16M 11/04 |
| | | | 248/274.1 |
| 6,450,166 B1 | 9/2002 | Lavimodiere et al. | |
| 6,619,288 B2 | 9/2003 | Demers et al. | |
| 6,837,238 B2 | 1/2005 | McDonald | |
| 7,004,437 B2 | 2/2006 | Bauer et al. | |
| 7,036,502 B2 | 5/2006 | Manne | |
| 7,040,581 B2 | 5/2006 | Noelke et al. | |
| 7,063,765 B2 | 6/2006 | Kudo et al. | |
| 7,089,941 B2 | 8/2006 | Bordewick et al. | |
| 7,124,755 B2 | 10/2006 | Van Hooser | |
| 7,267,305 B2 | 9/2007 | Kreuzer et al. | |
| 7,357,136 B2 | 4/2008 | Andrews et al. | |
| 7,453,585 B2 | 11/2008 | Dodge et al. | |
| 7,540,457 B2 * | 6/2009 | Oddsen, Jr. | F16M 11/04 |
| | | | 248/278.1 |
| 7,597,298 B2 | 10/2009 | Papendieck et al. | |
| 7,677,515 B2 * | 3/2010 | Oddsen, Jr. | F16M 11/04 |
| | | | 248/274.1 |
| 7,694,680 B2 | 4/2010 | Brichetto | |
| 7,744,043 B2 | 6/2010 | Otinger | |
| 7,975,693 B2 | 7/2011 | Geiselhart et al. | |
| 8,011,071 B2 | 9/2011 | O'Brien | |
| 8,181,918 B2 | 5/2012 | McCloud | |
| 8,282,050 B2 | 10/2012 | Georgey | |
| 8,360,058 B2 | 1/2013 | Ahearn et al. | |
| 8,534,618 B2 | 9/2013 | Mays | |
| 8,540,196 B1 | 9/2013 | Hodson | |
| 8,704,960 B2 * | 4/2014 | Weaver | B60R 11/0235 |
| | | | 192/107 C |
| 8,794,233 B2 | 8/2014 | Ahearn et al. | |
| 9,180,262 B2 * | 11/2015 | Cota | A61M 11/06 |
| 9,267,537 B2 * | 2/2016 | Plomteux | F16C 11/10 |
| 2002/0074463 A1 | 6/2002 | Nakamura | |
| 2003/0116167 A1 | 6/2003 | Van Hooser | |
| 2007/0045481 A1 | 3/2007 | Adams | |
| 2007/0295869 A1 | 12/2007 | Noelke et al. | |
| 2008/0053437 A1 | 3/2008 | Steiner et al. | |
| 2008/0078397 A1 | 4/2008 | Christianson et al. | |
| 2008/0185359 A1 | 8/2008 | Baxter | |
| 2008/0197256 A1 * | 8/2008 | Hirschhorn | F16M 11/04 |
| | | | 248/276.1 |
| 2009/0039210 A1 | 2/2009 | Shrivastava et al. | |
| 2009/0065005 A1 | 3/2009 | Ades | |
| 2009/0179117 A1 | 7/2009 | Thomas | |
| 2009/0230269 A1 * | 9/2009 | Dallarosa | A61B 18/201 |
| | | | 248/288.11 |
| 2012/0103326 A1 | 5/2012 | Karle et al. | |
| 2012/0285452 A1 | 11/2012 | Amirav et al. | |
| 2013/0174838 A1 | 7/2013 | Youngblood | |
| 2013/0306060 A1 | 11/2013 | Cota et al. | |
| 2015/0007812 A1 * | 1/2015 | Smith | B05B 7/0075 |
| | | | 128/200.21 |
| 2016/0030686 A1 * | 2/2016 | Cota et al. | A61M 11/06 |
| | | | 128/200.21 |

FOREIGN PATENT DOCUMENTS

| | | |
|---|---|---|
| WO | 2005112555 | 12/2005 |
| WO | 2007021969 | 2/2007 |

OTHER PUBLICATIONS

Kid O's Bear, #EO-KBN-4300, Mercury Medical, p. 270, commercially available at least as early as Aug. 2011.
OxyPhone, The Nebulizer Phone for Children, www.oxyphone.com; commercially available at least as early as May 2008.
International Search Report, Corresponding PCT Application No. PCT/US2014/043320, dated Oct. 15, 2014, 4 pages.

* cited by examiner

POSITIONABLE ELONGATED MEMBERS WITH MULTI-AXIS JOINTS

BACKGROUND

Devices and methods for delivering nebulized medicines are disclosed in International Application PCT/US13/39324, filed May 2, 2013, the complete disclosure of which is incorporated herein by reference. The devices disclosed therein include a positionable elongated member and a delivery tube, e.g., a length of flexible plastic tubing, disposed within the elongated member. Nebulized medicine is delivered through the delivery tube, and thus it is important that the delivery tube remain free from kinks or other constrictions regardless of the position of the positionable elongated member.

SUMMARY

Generally, this invention relates to devices and methods for delivery of a nebulized medicine to a patient. The devices disclosed herein may be configured for use in environments such as patients' homes, hospitals, doctors' offices, and nursing homes. The invention also relates to joints that may be used in such devices, and in particular to multi-axis joints that include both pivoting and swiveling functionality. In some cases, the joint can be moved to an open position in which it provides a continuous open slot for loading tubing into the joint, eliminating the need to thread tubing through a bore. The invention also features the use of the multi-axis joints described herein in other applications, particularly applications in which it is necessary to provide articulation while avoiding constriction of tubing disposed within the joint.

In one aspect, the invention features an apparatus comprising a multi-segment elongated member configured to support a tube and maintain a distal end of the tube in a desired position, and a multi-axis joint assembly disposed between segments of the elongated member to allow articulated relative movement of the segments.

Some implementations include one or more of the following features.

The multi-axis joint assembly may comprise a pivot joint and a swivel joint. The elongated member may define an open channel configured to receive the tube and the swivel joint may be configured to be moved between an open position, in which the swivel joint defines a channel that is colinear with the channel of the elongated member, and a closed position.

The pivot joint may include a female portion and a male portion having corresponding friction faces. The pivot joint may further comprise an adjustment device configured to allow the frictional force between the friction faces to be adjusted, e.g., a pair of caps that urge the friction faces together, and adjustment screws configured to adjust the pressure exerted by the caps.

The swivel joint may comprise a hub that is fixed relative to the pivot joint, and a collar that is rotatably mounted on the hub. In some cases, the hub and collar have corresponding friction faces. The swivel joint may further comprise an adjustment device configured to allow the frictional force between the friction faces of the hub and collar to be adjusted, e.g., one or more screws that draw the friction faces together. In some cases, one of the segments of the elongated member is mounted on the collar.

In some implementations, the multi-axis joint further comprises a second swivel joint, and the pivot joint is interposed between the two swivel joints. The hub may be joined to the pivot joint by a keyed engagement.

The apparatus may further include the delivery tube, which may be disposable, and the elongated member and the multi-axis joint may define a continuous open channel configured to allow the delivery tube to be removed and replaced. The apparatus may also include a base, on which a proximal end of the elongated member is mounted, and a nozzle at a distal end of the delivery tube.

In some cases, the elongated member includes at least three segments.

The invention also features multi-axis joints having any combination of the features disclosed herein.

DETAILED DESCRIPTION

Figure 1:
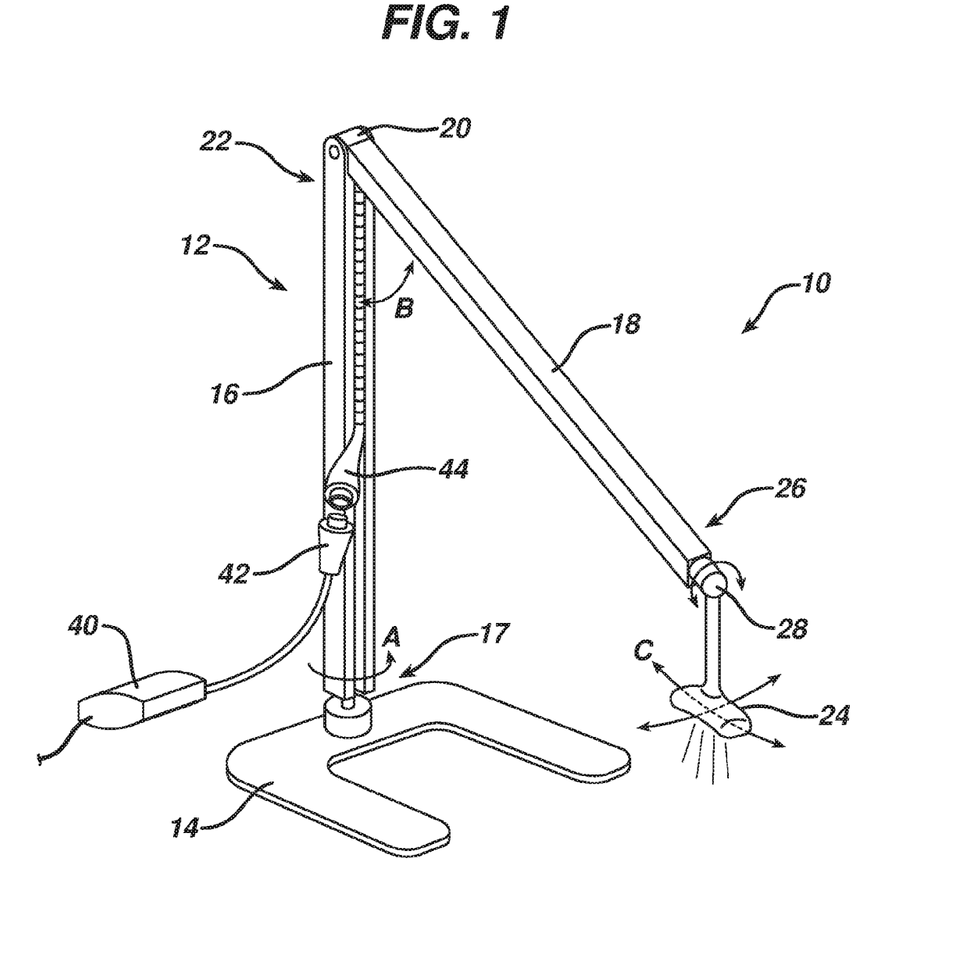
FIG. 1 is a perspective view of a device according to one embodiment, in which the device includes an articulated arm.

Referring to FIG. 1, in one embodiment a nebulized medicine delivery device 10 includes a positionable elongated member 12 supported by a base 14. In the embodiment shown in FIG. 1, the positionable elongated member 12 includes a first arm 16 which is coupled to the base 14 at its proximal end 17, and positionably coupled to a second arm 18 by an articulating joint 20 at its distal end 22. The features of this joint, which is shown diagrammatically in FIG. 1, will be discussed in further detail below with reference to FIGS. 2-7.

As indicated by arrow A, the proximal end 17 of the first arm is preferably mounted on the base 14 so that it can rotate (arrow A), and in some cases pivot, with respect to the base to enhance the overall positionability of the device. While rotation is preferred, if desired the first arm can be fixedly mounted to the base. In some implementations, the first arm is mounted on the base as disclosed in U.S. Ser. No. 13/934,565, filed Jul. 3, 2013, the full disclosure of which is incorporated herein by reference.

The articulating joint 20 (shown in FIG. 1 for simplicity as a hinge, but which is a multi-axis joint as discussed below) allows the first arm 16 and second arm 18 to pivot about the axis of the hinge in the manner indicated by arrow B.

The device 10 also includes a compressor 40 which delivers compressed gas (e.g., air) to a medicine cup 42 which, when the device is in use, contains a supply of medicine. The medicine cup 42 may be connected to the first arm 16 (as shown), or mounted within the arm or base, e.g., as disclosed in U.S. Ser. No. 13/934,565, filed Jul. 3, 2013, so as to hold the medicine cup in a stable, substantially vertical position during delivery of the medicine. This stable positioning of the medicine cup facilitates use of the device and enhances the effectiveness of the nebulizer. The compressor is connected to a power supply (not shown).

Figure 1A:
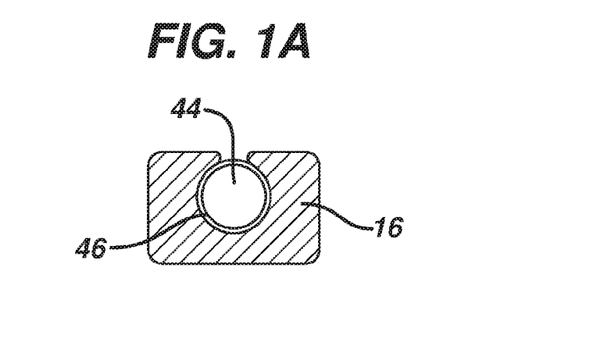
FIG. 1A is a cross-sectional view of an arm of the device shown in FIG. 1 with a delivery tube in place.

Medicine is nebulized in the medicine cup and then delivered to the patient via a delivery tube 44. As shown in detail in FIG. 1A, the delivery tube 44 is disposed in a channel 46 in the first arm 16. The second arm 18 includes a similar channel (not shown). These channels allow the tube to be held securely but removably within the positionable elongated member 12. Because the delivery tube is removable from the channel it can be easily replaced.

A nozzle 24 is mounted at the distal end 26 of the second arm, or to the distal end of the delivery tube, for delivery of the vaporized medicine to an area adjacent the patient's face. For example, delivery can be directed toward the patient's nose and mouth, so that the patient will receive the medicine regardless of whether she is breathing through her mouth or nose. Mounting of the nozzle may be by a pivotable connection 28, as shown, to provide fluid communication between the nozzle 24 and the delivery tube 44 while allowing the position of the nozzle to be finely adjusted as indicated by arrows C. Preferred types of nozzles are disclosed in International Application PCT/US13/39324, incorporated by reference above.

Figure 2:
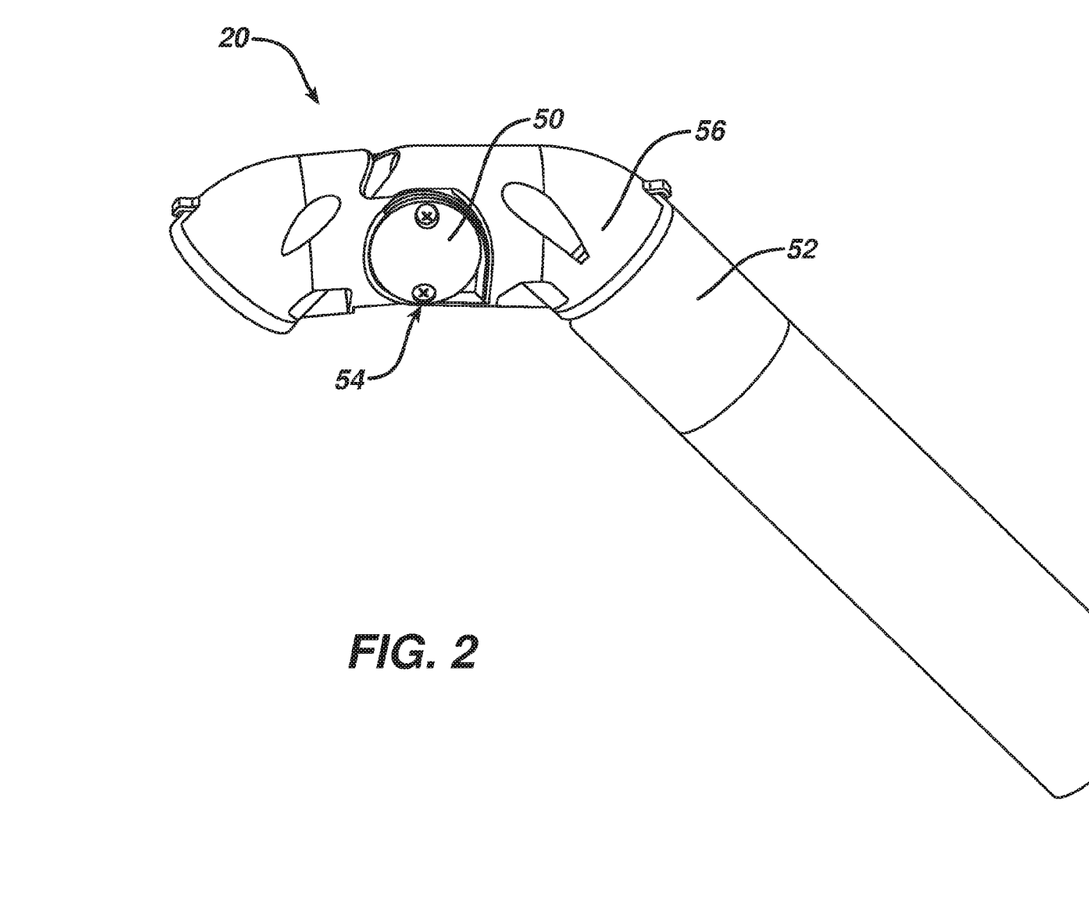
FIG. 2 is a perspective view of a multi-axis joint assembly according to one implementation.

Referring now to FIG. 2, the joint 20 is a multi-axis joint, which provides both a pivoting articulation, via pivot joint 50, and a swiveling motion, via swivel joint 52. The pivoting articulation is about an axis that is generally perpendicular to the long axis of the delivery tube, while the swiveling motion is about an axis that is generally parallel to the long axis of the delivery tube. The degree of friction (and conversely the ease of motion) of these joints are provided by a pivot joint adjustment screws 54 and a swivel joint adjustment screws 56, as will be discussed in further detail below.

Figure 3:
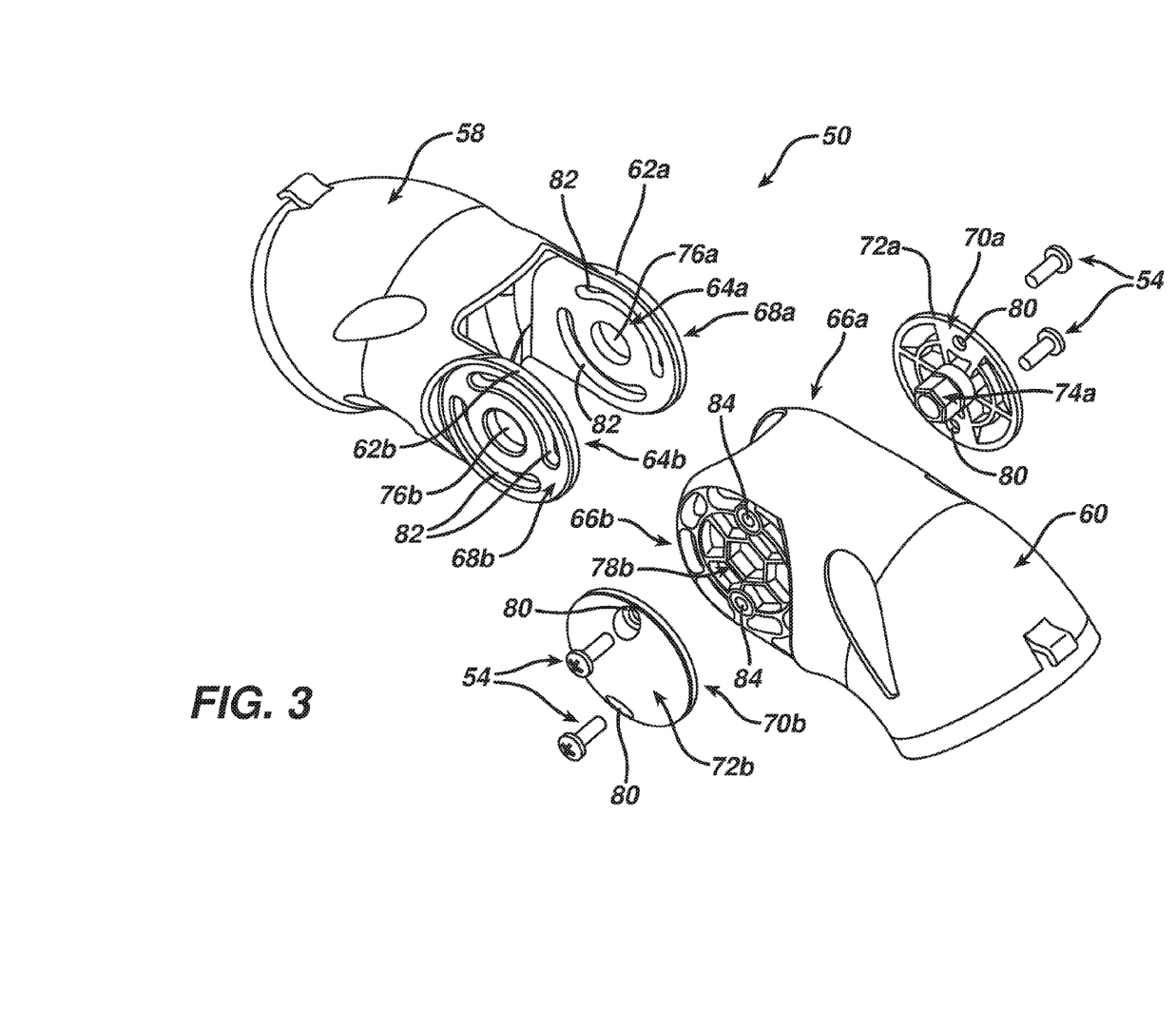
FIG. 3 is a partially exploded view of the pivot joint portion of the multi-axis joint assembly of FIG. 2.

The components of the pivot joint 50 are shown in more detail in FIG. 3. Pivot joint 50 includes a female portion 58 and a male portion 60. The male portion 60 is received between the two extending members 62a, 62b of the female portion, such that inner friction faces 64a, 64b of the female portion are in contact with adjacent friction faces 66a, 66b of the male portion. Outer friction faces 68a and 68b of the extending members contact friction surfaces 70a, 70b of a pair of pivot joint caps 72a, 72b. Each of the pivot caps includes a no-slip hex lock 74a When the joint is assembled, these hex locks extend through bores 76a, 76b in the extending members and are received into corresponding hexagonal openings 78a in the male portion 60, of which only opening 78b is visible in FIG. 3. The entire assembly is held together by a plurality of pivot joint adjustment screws 54. Screws 54 are received in threaded openings 80 in the pivot joint caps, through slots 82 in the extending members 62a, 62b, and into threaded openings 84 in the male portion. The extent to which the screws are tightened will determine the frictional force between the various friction faces, and thus how easily the female portion can pivot with respect to the male portion. Thus, the freedom of movement of the pivot joint can be easily adjusted both during manufacturing and by the end user simply by loosening or tightening the screws.

Figure 5A:
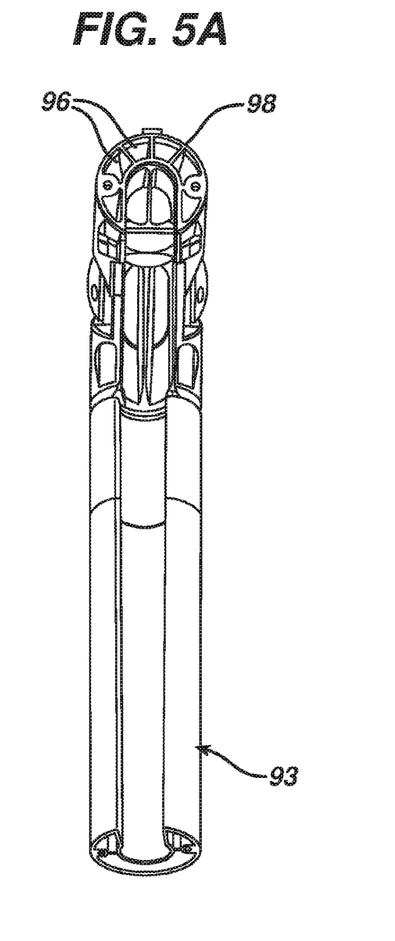
FIGS. 5A and 5B are perspective views of the multi-axis joint assembly of FIG. 2 with the swivel joint in open (FIG. 5A) and closed (FIG. 5B) positions.

As can be seen in FIG. 5A, in preferred implementations both the female and male portions of the pivot joint define an open channel, i.e., then are semi-cylindrical rather than cylindrical in shape. This feature facilitates easy insertion and removal of the delivery tube, allowing the end user to readily change out this disposable portion of the device.

The components of swivel joint 52 are shown in detail in FIGS. 4-7. The swivel joint performs two functions: (1) it provides a swiveling movement to the elongated member, about an axis generally parallel to the long axis of the delivery tube, as discussed above, and (2) it includes a portion that can be swiveled between an open position, in which the swivel joint defines an open channel that is colinear with that defined by the pivot joint (FIG. 5A), and a closed position (FIG. 5B). In some cases, in the closed position the swivel joint defines a closed cylinder.

The first function is particularly helpful when the elongated member of the delivery device includes more than one joint 20. If a plurality of joints are provided, then the swiveling function allows each segment of the elongated member to swivel relative to the adjacent segment, greatly increasing the degrees of freedom of the device. The second function allows the delivery tube to be easily inserted and removed from the swivel joint.

Figure 4:
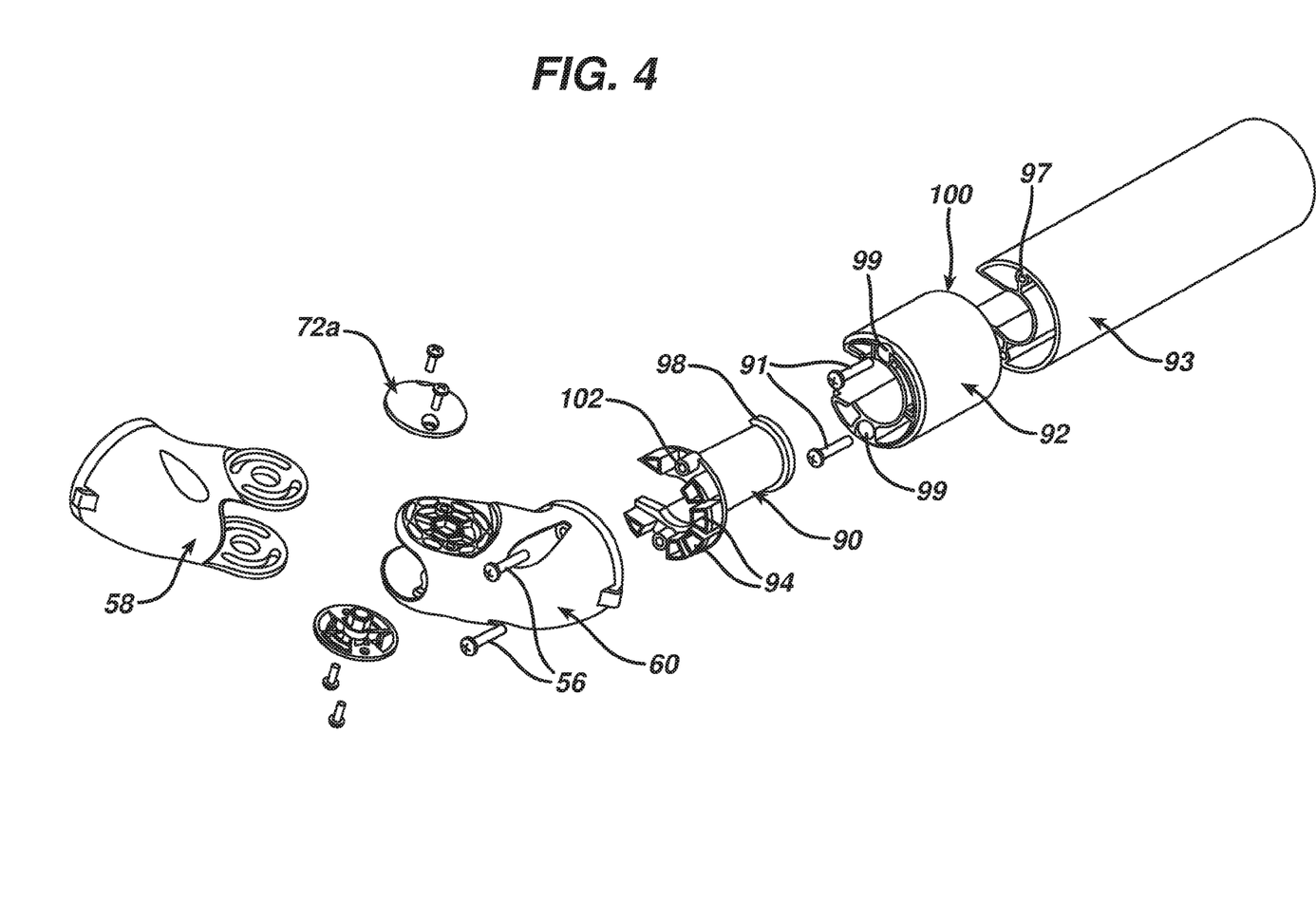
FIG. 4 is a fully exploded view of the multi-axis joint assembly of FIG. 2.
Figure 5B:
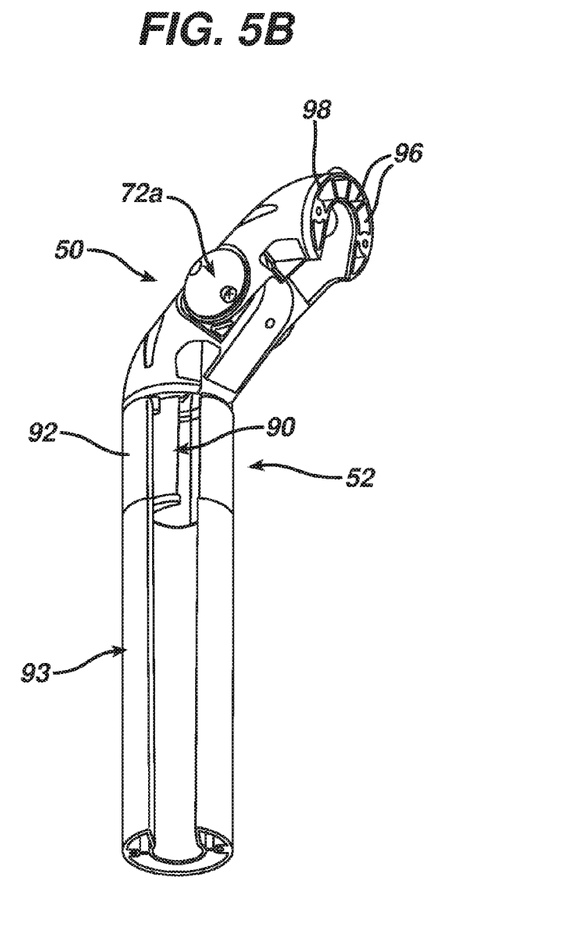
Figure 6:
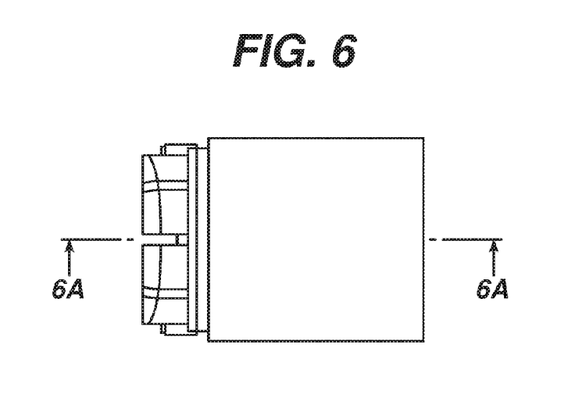
FIG. 6 is a side plan view of the swivel joint portion of the multi-axis joint assembly.
Figure 6A:
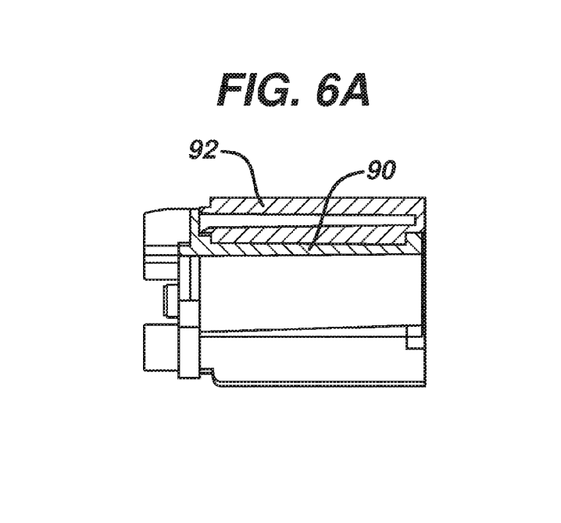
FIG. 6A is a cross-sectional view taken along line A-A in FIG. 6.
Figure 7:
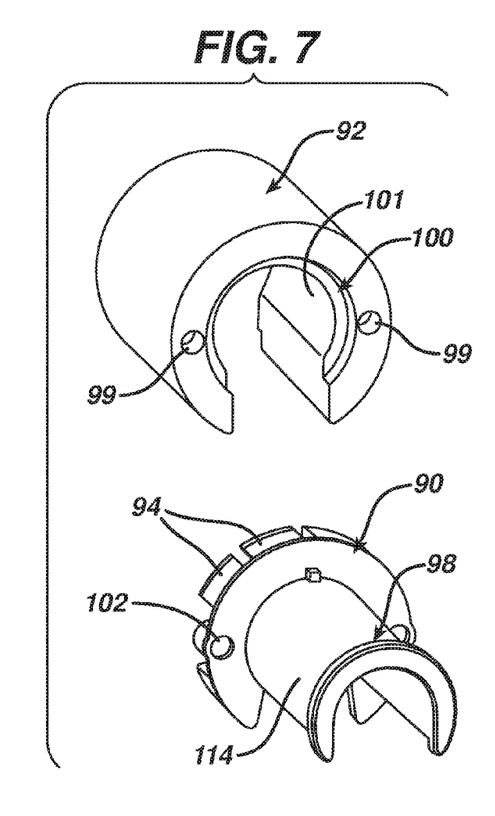
FIG. 7 is an exploded view of the swivel joint.

Referring to FIGS. 4 and 7, the swivel joint includes a swivel joint hub 90 and a swivel joint collar 92. The swivel joint hub 90 includes a plurality of teeth 94 at one end, which are configured for keyed engagement with corresponding openings in the end surface of the male portion of the pivot joint. (These openings, not shown, are similar to openings 96 in face 98 of the female portion, as shown in FIGS. 5A-5B.)

An elongated member 93 is fixedly attached to the swivel joint collar, e.g., by screws 91 extending through throughholes 99 (FIG. 7) in the swivel joint collar 92 and into corresponding threaded openings 97 (FIG. 4) in the elongated member.

Because of its keyed attachment to the male portion of the pivot joint, the swivel joint hub 90 is fixed relative to the pivot joint. The swivel joint collar 92 is positioned on the swivel joint hub for rotation relative to the swivel joint hub 90, thus allowing the elongated member 93 to swivel relative to the pivot joint. The freedom of rotation is determined by adjusting the normal force between friction face 98 of the swivel joint hub and friction face 100 of the swivel joint collar (best seen in FIG. 7), resulting in increased or decreased friction. The frictional force is adjusted by loosening or tightening screws 56 which extend through screw bosses 102 and draw the swivel joint hub toward the pivot joint (see arrow in FIG. 6A) thereby generating frictional force at the frictional interface (FIG. 6A) between the two friction faces.

Figure 8:
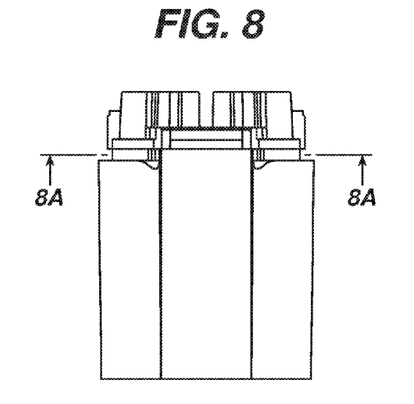
FIG. 8 is a side plan view of the swivel joint.
Figure 8A:
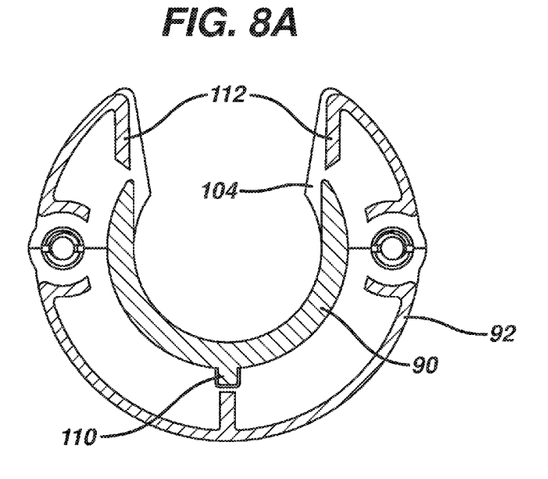
FIG. 8A is a cross-sectional view taken along line A-A in FIG. 8.
Figure 8B:
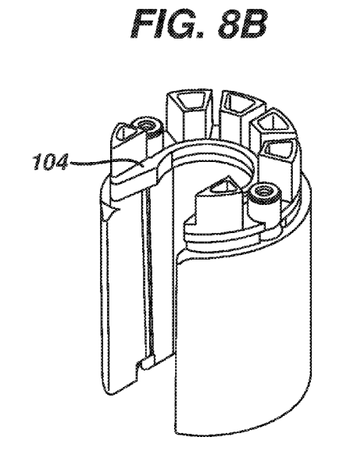
FIG. 8B is a perspective view.

Referring to FIG. 8, the swivel joint may include features that limit its rotation and/or serve to prevent the hub from coming out of the collar when the swivel joint is in its open position.

To limit rotation, e.g., to about 135 degrees or less, in some implementations a rotation stop tab 110 is provided on the swivel joint hub 90. This tab interferes with one of a pair of collar stop limit features 112 on the swivel joint collar at the desired limit of rotation in each direction.

To prevent separation of the hub from the collar the cylindrical bore of the hub 101 and the cylindrical shaft 114 have surfaces that comprise more than 180° of contacting surface. This surface acts to retain the collar and hub together in all positions as the joint rotates.

If desired, a second swivel joint (not shown) can be provided for attachment to the female portion of the pivot joint, using the openings 96, in which case a second elongated member would be fixedly attached to the swivel joint hub of the second swivel joint. Alternatively, if swiveling motion is not desired between the female portion of the pivot joint and the attached elongated member, the elongated member can be fixedly attached directly to the female member.

Other Embodiments

A number of embodiments have been described. Nevertheless, it will be understood that various modifications may be made without departing from the spirit and scope of the disclosure.

For example, while it is generally preferable to combine the pivoting and swiveling features described above in a single multi-axis joint, in some cases these features may be used individually, to provide a pivot joint or a swivel joint.

Moreover, while the multi-axis joint has been discussed above in the context of its use in the delivery of nebulized medicines, the multi-axis joint may be used in a variety of other applications, such as in other medical devices where multi-axis movement would be useful, particularly where it is important to be able to remove and replace tubing that runs through the joint. The multi-axis joint could also be used in other applications in which a precise and flexible positioning and directional control of delivery of a gas or fluid is desired, e.g., in industrial applications such as painting or welding.

Additionally, in some implementations, for example in applications not requiring an open channel for insertion of tubing, the joint could include cylindrical members rather than members that are shaped to define an open channel.

Accordingly, other embodiments are within the scope of the following claims.

What is claimed is:

1. An apparatus comprising:
- a multi-segment elongated member configured to support a tube and maintain a distal end of the tube in a desired position, and
- a multi-axis joint assembly, comprising a pivot joint and a swivel joint, disposed between segments of the elongated member to allow articulated relative movement of the segments,
- wherein the elongated member defines an open channel configured to receive the tube and the swivel joint is moved between an open position, in which the swivel joint defines a channel that is colinear with the channel of the elongated member, and a closed position.

2. The apparatus of claim 1 wherein the pivot joint comprises a female portion and a male portion having corresponding friction faces.

3. The apparatus of claim 2 wherein the pivot joint further comprises an adjustment device configured to allow the frictional force between the friction faces to be adjusted.

4. The apparatus of claim 3 wherein the adjustment device comprises a pair of caps that urge the friction faces together, and adjustment screws configured to adjust the pressure exerted by the caps.

5. The apparatus of claim 1 wherein the swivel joint comprises a hub that is fixed relative to the pivot joint, and a collar that is rotatably mounted on the hub.

6. The apparatus of claim 5 wherein the hub and collar have corresponding friction faces.

7. The apparatus of claim 6 wherein the swivel joint further comprises an adjustment device configured to allow the frictional force between the friction faces of the hub and collar to be adjusted.

8. The apparatus of claim 7 wherein the adjustment device comprises one or more screws that draw the friction faces together.

9. The apparatus of claim 5 wherein one of the segments of the elongated member is mounted on the collar.

10. The apparatus of claim 5 wherein the hub is joined to the pivot joint by a keyed engagement.

11. The apparatus of claim 1 further comprising the tube.

12. The apparatus of claim 11 wherein the tube comprises a disposable delivery tube.

13. The apparatus of claim 12 wherein the elongated member and the multi-axis joint define a continuous open channel configured to allow the delivery tube to be removed and replaced.

14. The apparatus of claim 1 wherein the elongated member includes at least three segments.

15. The apparatus of claim 1 further comprising a base on which a proximal end of the elongated member is mounted.

16. The apparatus of claim 12 further comprising a nozzle provided at a distal end of the delivery tube.

17. An apparatus comprising:
- a multi-segment elongated member configured to support a tube and maintain a distal end of the tube in a desired position, and
- a multi-axis joint assembly, comprising a pivot joint and a swivel joint, disposed between segments of the elongated member to allow articulated relative movement of the segments,
- wherein the swivel joint comprises a hub that is fixed relative to the pivot joint, and a collar that is rotatably mounted on the hub, the hub and collar having corresponding friction faces, and
- wherein the swivel joint further comprises an adjustment device configured to allow the frictional force between the friction faces of the hub and collar to be adjusted.

18. An apparatus comprising:
- a multi-segment elongated member configured to support a tube and maintain a distal end of the tube in a desired position, and
- a multi-axis joint assembly, comprising a pivot joint and a swivel joint, disposed between segments of the elongated member to allow articulated relative movement of the segments,
- wherein the swivel joint comprises a hub that is fixed relative to the pivot joint, and a collar that is rotatably mounted on the hub, and the hub is joined to the pivot joint by a keyed engagement.

19. An apparatus comprising:
- a disposable delivery tube,
- a multi-segment elongated member configured to support the disposable delivery tube and maintain a distal end of the tube in a desired position, and
- a multi-axis joint assembly disposed between segments of the elongated member to allow articulated relative movement of the segments,
- wherein the elongated member and the multi-axis joint define a continuous open channel configured to allow the delivery tube to be removed and replaced.

20. The apparatus of claim 19 wherein the multi-axis joint assembly comprises a swivel joint and a pivot joint.

21. The apparatus of claim 20 wherein the pivot joint comprises a female portion and a male portion having corresponding friction faces.

22. The apparatus of claim 21 wherein the pivot joint further comprises an adjustment device configured to allow the frictional force between the friction faces to be adjusted.

23. The apparatus of claim 22 wherein the adjustment device comprises a pair of caps that urge the friction faces together, and adjustment screws configured to adjust the pressure exerted by the caps.

24. The apparatus of claim 20 wherein the swivel joint comprises a hub that is fixed relative to the pivot joint, and a collar that is rotatably mounted on the hub.

25. The apparatus of claim 24 wherein the hub and collar have corresponding friction faces.

26. The apparatus of claim 25 wherein the swivel joint further comprises an adjustment device configured to allow the frictional force between the friction faces of the hub and collar to be adjusted.

* * * * *